(12) United States Patent
Filatov et al.

(10) Patent No.: US 8,722,081 B2
(45) Date of Patent: May 13, 2014

(54) HEMOSTATIC TEXTILE MATERIAL

(76) Inventors: Vladimir N. Filatov, Moscow (RU);
Vladimir Ryltsev, Moscow (RU);
Zidkiyahu Simenhaus, Galil Elyon (IL)

( * ) Notice: Subject to any disclaimer, the term of this patent is extended or adjusted under 35 U.S.C. 154(b) by 700 days.

(21) Appl. No.: 11/872,072

(22) Filed: Oct. 15, 2007

(65) Prior Publication Data
US 2008/0181936 A1 Jul. 31, 2008

(30) Foreign Application Priority Data

Oct. 26, 2006 (IL) .......................................... 178867

(51) Int. Cl.
| | |
|---|---|
| A61L 15/28 | (2006.01) |
| A61K 31/717 | (2006.01) |
| A61L 15/42 | (2006.01) |
| A61K 31/198 | (2006.01) |
| A61K 31/192 | (2006.01) |
| A61K 33/38 | (2006.01) |
| A61F 13/64 | (2006.01) |
| A61F 13/00 | (2006.01) |
| A61K 9/70 | (2006.01) |
| A61L 15/32 | (2006.01) |
| C08L 1/04 | (2006.01) |
| C08L 5/08 | (2006.01) |

(52) U.S. Cl.
CPC . *A61K 9/70* (2013.01); *A61L 15/42* (2013.01); *A61L 15/28* (2013.01); *A61K 31/717* (2013.01); *A61F 13/00085* (2013.01); *A61L 15/32* (2013.01); *C08L 1/04* (2013.01); *C08L 5/08* (2013.01); *A61K 31/198* (2013.01); *A61K 31/192* (2013.01); *A61K 33/38* (2013.01); *D10B 2509/022* (2013.01); *A61L 2400/04* (2013.01)
USPC ............... 424/445; 514/2.4; 514/4.9; 514/55; 514/57; 514/572; 424/619; 8/116.4

(58) Field of Classification Search
None
See application file for complete search history.

(56) References Cited

U.S. PATENT DOCUMENTS

| | | | | |
|---|---|---|---|---|
| 4,572,906 A | * | 2/1986 | Sparkes et al. ................ | 424/445 |
| 5,484,913 A | | 1/1996 | Stilwell et al. | |
| 5,538,500 A | * | 7/1996 | Peterson ......................... | 602/48 |
| 6,500,799 B2 | | 12/2002 | Filatov et al. | |
| 6,762,337 B2 | * | 7/2004 | Boukanov et al. .............. | 602/53 |
| 6,861,570 B1 | * | 3/2005 | Flick ............................... | 602/41 |

(Continued)

FOREIGN PATENT DOCUMENTS

| | | |
|---|---|---|
| DE | 40 00 797 | 7/1991 |
| EP | 0468114 | 1/1992 |

(Continued)

OTHER PUBLICATIONS

Pusateri et al., Journal of Trauma—Injury, Infection, and Critical Care, 54(1) 177-182 (2003).*

*Primary Examiner* — Kortney L Klinkel
*Assistant Examiner* — Lisbeth C Robinson
(74) *Attorney, Agent, or Firm* — Bachman & LaPointe, P.C.

(57) ABSTRACT

A hemostatic textile material to stop bleeding comprising a dialdehyde cellulose (DAC) carrier wherein the degree of oxidation of the dialdehyde cellulose varies from about 1.5% to 12%; and a blood coagulation factor selected from the group consisting of chitosan and gelatin; the blood coagulation factor being chemically immobilized thereon; and further optionally comprising a bacteriolytic agent selected from the group consisting of a lysozyme enzyme, silver nitrate, and chlorhexidine; and further optionally comprising a selected component that prevents hemolysis, the component selected from the group consisting of tranexamic acid or ε-aminocaproic acid chemically immobilized thereon.

19 Claims, 2 Drawing Sheets

(56) References Cited

U.S. PATENT DOCUMENTS

| | | |
|---|---|---|
| 2003/0078209 A1 | 4/2003 | Schmidt |
| 2004/0101546 A1* | 5/2004 | Gorman et al. ............... 424/445 |
| 2004/0193088 A1* | 9/2004 | Looney et al. ................. 602/48 |
| 2004/0243044 A1* | 12/2004 | Penegor et al. ................ 602/48 |
| 2006/0013863 A1* | 1/2006 | Shalaby et al. ............... 424/443 |

FOREIGN PATENT DOCUMENTS

| | | | |
|---|---|---|---|
| GB | 2 240 040 | | 7/1991 |
| RU | 2 062 113 | | 6/1996 |
| RU | 2 235 539 | | 9/2004 |
| RU | 2235539 | * | 9/2004 |

* cited by examiner

HEMOSTATIC TEXTILE MATERIAL

BACKGROUND OF THE INVENTION

The present invention relates to the field of pharmacology. More particularly the present invention relates to a hemostatic textile material to stop bleeding and to methods for producing blood-arresting (hemostatic) preparations on a partially oxidized cellulose base.

Hemostatic textile materials are well known. European patent application No. 1,153,620 describes a hemostatic dressing for preventing any bacterial contamination of a wound and made of oxidized cellulose SURGIGEL® (Johnson & Johnson) containing from 1 to 10,000 p.p.m. of ferric ions ($Fe3^+$). European patent application No. 468,114 describes a soluble hemostatic material available as a fabric made of cellulose which has first been oxidized with monochloro-acetic acid and sodium hypochlorite to introduce carboxylic groups COOH on to the cellulose substrate. European patent application No. 659,440 describes a method for preparing a hemostatic material on an oxidized cellulose base comprising 0.5 to 4.0% of calcium as well as thrombin, fibrinogen and/or an antifibrinolytic agent.

One of the drawbacks of these known methods is the degree of oxidation of the textile fabric. The use of cellulose, having a low and/or mild degree of oxidation, requiring the conversion of $CH_2OH$ groups into carboxylic groups (COOH) results in precluding any possibility of obtaining a material capable of strongly and effectively binding other components thereto. Only calcium ions become bound with COOH— groups with the intermediacy of ionic forces whereas all other components present as a physical (mechanical) mixture.

In laid-open German Patent No. 4000797, C 12N 11/02, Jul. 18, 1991; and GB Patent No. 2,240,040 A, dated Jul. 24, 1991; and Russian Patent No. 2062113, A 61 L 15/38 Jun. 20, 1996, there are mentioned carriers which contain reactive functional groups that are used for preparing materials containing immobilized enzymes having prolonged action for treating wounds and burns.

Known in the art according to U.S. Pat. No. 6,500,799 B2 dated Dec. 31, 2002 is a method for preparing a carrier which comprises aldehyde functional groups having 0.208% w/w-corresponding to 0.026 mg-equiv.- to 0.48 w/w-corresponding to 0.06 mg.-equiv. per gram of carrier, for binding enzymes and other bioactive substances.

Russian Patent No. 2,235,539 describes a method for preparing a powdered material to arrest bleeding, which comprises the stages of mixing, in an aqueous solution, a carrier, i.e., partially oxidized cellulose, with blood coagulation factors, i.e., thrombin and fibrinogen, supplemented with gelatin, ε-aminocaproic acid and lysozyme. Dialdehyde cellulose in the form of a fabric is used as a partially oxidized cellulose having the degree of oxidation (i.e., the content of aldehyde groups) of from 4% to 6%, with the ratios between the components being as follows:

| | |
|---|---|
| dialdehyde cellulose | 1 g; |
| fibrinogen | 18-22 mg; |
| gelatin | 27-33 mg; |
| ε-aminocaproic acid | 45-55 mg; |
| lysozyme | 9.5-10.5 mg; |
| thrombin | 350 Units; and |
| water | 6.5 ml. |

The components are combined so as to obtain a complete covalent binding of the therapeutic substances with the dialdehyde cellulose. This is followed by drying and grinding to produce a powder. The final product, which contains fibrinogen and thrombin, is disadvantageous due to the premature conversion of the fibrinogen into a fibrin clot through interaction with the thrombin. In such cases the product(s) will be rendered useless.

The known method of U.S. Pat. No. 2,235,539, which describes how to overcome this major problem, has significant shortcomings. The proposed solution is most complicated and utilizes a disjointed production process. In order to prevent thrombin from activating fibrinogen, the preparation is manufactured in two stages. Thus a solution with half of the total amount of water and fibrinogen, ε-aminocaproic acid and a half of the total amount of gelatin is prepared. Half the amount of the dialdehyde cellulose textile fabric is immersed in the above mentioned solution, for 3-4 hours, pressed and air-dried.

A separate solution is prepared that contains the remaining amount of water, thrombin, lysozyme and the remaining amount of gelatin. The remaining dialdehyde cellulose is immersed into this separately prepared solution, for 3-4 hours. The semi-finished products are pressed out, air-dried and ground together for immediate use only.

It is well known that products containing animal or human proteins such as thrombin and fibrinogen, carry the risk of blood-born transmittable agents, especially if these products have not undergone viral inactivation procedures.

In respect to the safety of patients and medical personnel as well, it is a common desire to use preparations, which are free of blood components, thus avoiding the hazard of infection from blood-born transmittable agents.

Furthermore, the dialdehyde textile produced according to the above mentioned patents, because of lack of aldehyde functional groups or functional groups not equally spread, will fail to achieve the goal of covalently binding only 85-90% of the total amino groups into the fabric; so that 10-15% of gelatin and tranexamic acid or ε-aminocaproic acid, chitosan, lysozyme and/or other antimicrobial ingredients as described hereinbefore, can be adsorbed on the carrier so as to ensure the presence of a sufficient quantity thereof for arresting severe and fast bleeding, and for stabilizing the clotting, and avoiding fibrinolysis, as proposed by the present invention.

SUMMARY OF THE INVENTION

With the above state of the art in the mind, it is the objective of the present invention to provide such a hemostatic material base on partially oxidized cellulose textile, which would be free of any of the above mentioned drawbacks, and to propose a method for making the same.

In particular, the present invention provides a medical dressing without fibrinogen and without thrombin.

According to the present invention there is now provided a dry, disposable, polymeric product, which contains respectively a variety of combinations of the following components: dialdehyde cellulose; gelatin; chitosan; tranexamic acid, or a substitute: ε-aminocaproic acid; lysozyme, chlorhexidine (CHX and/or CHG), or silver nitrate.

Dialdehyde Cellulose:

The new proposed dialdehyde cellulose (DAC) carrier is suitably designed so as to meet the requirements of the active components of the present hemostatic material and especially to enable the binding of said components at the herein determined required ratio, and to ensure the appropriate release of said components as described hereinafter.

Gelatin:

Gelatin is a collagen product, which is manufactured by way of a boiling process or through the use of salts. During the production process a breaking down of the triple helix of the collagen occurs. The derivative which is produced is a gel-like, water-soluble gelatin comprising separate α-chains rich in lysine and proline (or hydroxyproline) residues. The latter amino acids are also known to exert a wound-healing action.

Gelatin adheres well to other proteins and is well known as a hemostatic agent. It is used as a hemostatic factor in some biological glues. It should be noted that in the new hemostatic material of the present invention, the gelatin, which is incorporated into and onto the carrier, is immobilized. It is bonded by chemical covalent azomethine-type bonds, formed between the aldehydic groups of the carrier and the amino groups of gelatin. Hence, the gelatin improves bonding of the other active ingredients with the carrier and potentiates the hemostatic action of the material.

Chitosan:

Chitosan, which is also a hemostatic component, functions as a factor for stopping bleeding. (Hereinafter referred to as a stop bleeding factor.) Furthermore the Chitosan binds all other different protein components of the hemostatic device, of both exogenous and endogenous origin, to form a complex, i.e., it integrates these protein components into a system. It also enhances the adhesion of the new proposed device to the wound surface, thus contributing to the efficacy of the product and to blood coagulation.

Tranexamic Acid, or a substitute: ε-aminocaproic acid:

Immobilized tranexamic acid (or, its substitute the immobilized ε-aminocaproic acid) is beneficial when the clot-thrombus adhesion to the wound surface is weak and recurrence of breaking-off with bleeding occurs.

The immobilized tranexamic acid, and/or its substitute the immobilized ε-aminocaproic acid, suppresses the fibrinolysis process by blocking plasminogen activators and partly suppressing the action of plasmin, thereby reducing the risk of hemolysis of the clot-thrombus that has been rapidly formed at the site of bleeding.

Owing to the fact that the new hemostatic material is supplemented with the above mentioned components to suppress fibrinolysis, the clot-thrombus and its adhesion to the wound surface are more stable and safe. Thus, the incidence of pathological conditions, such as thrombophlebitis, which poses a threat to the blood vessels of the heart or brain, and cause infarct or respective damage, is reduced and/or even avoided.

Lysozyme and/or other antimicrobial ingredients:

Lysozyme is a protein with bacteriolytic activity. Its function is to ensure the sterility of the blood clot. Similarly, lysozyme is attached to the carrier with covalent azomethine-bonds.

According to the present invention only 5 mg of lysozyme per 1 (one) gram of the carrier is sufficient to ensure complete antimicrobial activity and sterility of the material—a reduction of the amount of lysozyme by a factor of 2 (two) in comparison to the prior art.

Chlorhexidine:

Chlorhexidine (CHX and/or CHG), which is an antiseptic agent, is used in some embodiments as an antimicrobial substitute for the lysozyme. In some other embodiments the chlorhexidine is exerting a co-operative bactericidal activity together with lysozyme.

Silver:

Silver is another antimicrobial substitute that has been incorporated in some embodiments.

The present invention provides a rapid and efficient hemostatic device(s) due to the ingredients chemically immobilized on a textile substrate having aldehyde groups. It should be pointed out that the blood clot formed after the application of the hemostatic material is, in its structure and functional properties, similar to the connective tissue of the natural epidermis, especially to its papillary layer(s) which is composed of soft fibrous connective tissue comprising thin bundles of collagen, elastic and reticular fibers.

The exogenous components of the present invention, i.e., the dialdehyde cellulose, the chitosan and the gelatin, each component in itself being a hemostatic ingredient, upon coming in contact with blood, act in synergy as coagulation factors and also as stimulators that accelerate the interaction between the endogenous thrombin and fibrinogen. The interaction between the thrombin and the fibrinogen creates fibrin, which is the natural clotting factor. As a result the clotting process is accelerated.

The gelatin, a product of collagen hydrolytic cleavage, acting as collagen fibers, together with the fibrinolysis ingredients, i.e., the tranexamic acid or its substitute the ε-aminocaproic acid, imparts stability to the blood clot.

A thrombus is formed as a result of endogenous thrombin and fibrinogen interaction, which acts as elastic and reticular fibers, making the blood clot elastic.

The lysozime, or its substitutes the chlorhexidine or the silver, which are antimicrobial components, keeps the wound site free of microorganisms.

One more salient feature of the proposed invention is the unusual proportion between the amount of aldehyde groups of the carrier and that of the amino groups of the immobilized blood coagulation factors. The incorporated aldehyde groups bind covalently only 85-90% of the total amino groups. Consequently, 10-15% of lysozyme, gelatin and ε-aminocaproic acid are adsorbed on the carrier. Upon application to a bleeding surface, some blood seeps through the hemostatic material into the absorbing layer carrying away chemically unbound ingredients. As a result, a blood clot is formed according to the same mechanism, which is structurally related to the clot on the wound surface. This improves drastically the stability of the clot and its adhesion to the wound surface.

An additional advantage of the new material manufactured according to the present invention, in respect to the efficacy and safety of patients and medical personnel as well, derives from excluding the thrombin and fibrinogen from the formula of the preparations. Excluding the use of animal or human proteins from the preparations, enables the manufacturing of products, which are free of blood components, thus avoiding the hazard of infection by blood borne transmittable agents.

Such products, free of blood components, need not to undergo viral inactivation procedures thus simplifying production.

Furthermore excluding thrombin and fibrinogen, which are extremely sensitive ingredients to high temperature, from the formulation, enables reduction of the amount of lysozyme by a factor of 2; and also enables the incorporation of some other substitute bactericidal ingredients such as Argentums, Chlorhexidine, or any of the quaternary family, into and onto the carrier of the new proposed material, which can then be dried in a continuous process at 50° C.-120° C.

The hemostatic material is composed of several layers, e.g.:

1) a layer which contains the hemostatic ingredients as described in sample 5 hereinafter;
2) any absorbing layer; and, 3) optionally any elastic bandage, which is provided with elements of fixation to a human body, as described hereinafter, which material is sealed in polyethylene bags and gamma sterilized.

A preferred embodiment of the present invention is produced by adding an absorbent layer, e.g., by sewing as hereinafter described in example 7. The composite dressing is comprised of 3 layers as follows:
1) The dialdehyde cellulose fabric that contains ϵ-aminocaproic acid (5 g), and lysozyme (0.5 g);
2) The fabric that comprises the Chitosan (3 g) and chlorhexidine; and
3) The absorbent layer.

It is well known, that with injuries which affect not only capillaries but also arteries, the hemostatic action of the blood coagulation factors, under certain circumstances, might not be enough to stop bleeding rapidly. By and large in such cases, pressure is applied to the hemostatic device, which is applied on top of the bleeding wound.

The present invention also provides a self sliding dressing to be used in such cases. The new hemostatic textile material is attached by lamination to a woven or non-woven absorbing layer made of natural polymers such as cotton, or man made polymers such as viscose fibers, or a blend of polyester and viscose fibers, woven or non-woven, such as a non-woven dressing; either coated or not coated on both sides with a porous film made of ethylene-methacrylic acid copolymer, or a polyethylene fabric to shape a structure of a combined pad, by lamination or by sewing or by welding.

Two strips are attached to the back side of the combined pad, as described hereinafter with regard to FIG. 1, to enable the sliding attachment of the combined pad on any elastic bandage of any width. The elastic bandage acts as the pressure tool.

To affix the bandage, a velcro strip or hooks are attached to the remote end of an elastic bandage, said bandage being of about 40 cm or so in length. To the other end of the dressing, a strip of adhesive tape of about 5 cm in any width or requested length is attached. In most cases, the adhesive tape enables the injured party to secure the proposed stop-bleeding device to the wound site by himself.

The adhesive strip is applied to a healthy skin area adjacent the wound. The combined pad, which comprises both a hemostatic and an absorbing layer is slid and placed so as to cover the bleeding wound site. The degree of compression can be adjusted by increasing the tension of the elastic bandage. Wrapping the elastic bandage two or three times around the combined pad will create the necessary pressure necessary to facilitate a fast stoppage of bleeding effect and will also affix the combined hemostatic dressing to the wound site. It will be secured by a velcro tape, by hooks, or by a simple knot.

In summary, dialdehyde cellulose, chitosan and gelatin, accelerate the stoppage of bleeding, and tranexamic acid and/or ϵ-aminocaproic acid prevents fibrinolysis. These components promote coagulation, i.e., the formation of blood clots. Lysozyme, or argentums, or chlorhexidine provide antimicrobial activity and maintain sterility of the wound site and the blood clots as well. The readily absorbing layer absorbs excessive fluid from the wound, while the elastic bandage exerts compression and pressure to the injured area, and constricts vascular lumina risk.

Preparation of the Suitable Dialdehyde Cellulose

A textile material carrier which comprises aldehyde functional groups having 0.050 mg-equiv. per one gram of carrier to about 0.085 mg-equiv. per one gram of carrier, is required in order to bind the ϵ-aminocaproic acid or tranexamic acid, the gelatin and other biological or chemical substances as described herein below.

The oxidation method for the preparation of the textile material carrier according to the present invention, is carried out as follows: the textile fabric is immersed in a solution containing functional groups. By utilizing a wringer of two or three rollers, or a similar type press, the textile material is pressed. The excess solution is pressed out and the material is dried. Consequently, the functional groups are spread equally and uniformly onto and into the fabric. The resulting material is dried by utilizing forced air in a continuous process as described hereinafter:
(1) The air is filtered and cleaned;
(2) The clean air is forced into a freezing chamber at a temperature below −20° C.;
(3) The cleaned cold material is forced, at a temperature of about −15° C. to −10° C. to a heating chamber; and
(4) The treated material is then dried by utilizing a blowing chamber, a drying oven, or a vacuum chamber at 35° C.-100° C. as designed. The speed of the process is monitored.

Thus the present invention inter alia provides a method for preparing a wound dressing, comprising activating a textile carrier to form between about 1.5% w/w, corresponding to 0.1875 mg-equiv. to 12% w/w, corresponding to 1.5 mg-equiv. of aldehyde groups per gram of carrier.

The textile carrier with said aldehyde groups attached thereto is then brought into contact with a solution containing gelatin, ϵ-aminocaproic acid or tranexamic acid and other biological or chemical substances, as described herein, for impregnating or coating said fabric. The impregnated fabric is then pressed by a wringer, or a padder, between two or three rollers, and the solvent is separated from the treated textile material by pressing, squeezing, evaporation, or centrifugation, etc. The obtained material is dried by utilizing forced hot air, oven drying, vacuum chamber, etc., at 35° C.-120° C. The speed of the process is monitored.

More specifically, the fabric is immersed at room temperature in a solution, which contains functional groups. The ratio of the solution weight to the carrier weight is about 3.3. In a continuous process the excess solution is pressed out and the carrier material(s) is dried utilizing a wringer with two or three rollers at 25 Kg-35 Kg pressure per 1 sq. cm. The excess solution is pressed out spreading the active compounds uniformly into the volume of the textile carrier and on the surface of the fabric. Thus the fabric is partially dried. The carrier material(s) is further dried by utilizing a dryer, i.e., a hot air blowing chamber, a hot dram chamber heated from about 35° C. up to 100° C.; a vacuum chamber or by being lyophilized. Then the material is immersed in a tub containing a solution of gelatin, ϵ-aminocaproic acid, or tranexamic acid, and other biological or chemical substances as described herein below at a ratio of solution weight to carrier of 6.5. The impregnated fabric is then pressed out by a wringer between two rollers. The ingredients hereinabove described are equally and uniformly incorporated and spread into the volume of the textile carrier and onto the surface of the fabric, while the excessive solvents are pressed out. The obtained material is again dried by utilizing forced hot air, oven drying at 35° C.-100° C., or vacuumed in a vacuum chamber and/or lyophilized. The speed of the drying process is synchronized.

In a further aspect of the present invention there is now provided a hemostatic textile material to stop bleeding comprising:

a) a dialdehyde cellulose (DAC) carrier wherein the degree of oxidation of the dialdehyde cellulose varies from about 1.5% to 12%; and
b) a blood coagulation factor selected from the group consisting of chitosan and gelatin; said blood coagulation factor being chemically immobilized thereon; and further optionally comprising
c) a bacteriolytic agent selected from the group consisting of a lysozyme enzyme, silver nitrate, and chlorhexidine; and further optionally comprising
d) a selected component that prevents hemolysis, said component selected from the group consisting of tranexamic acid or $\epsilon$-aminocaproic acid chemically immobilized thereon.

In preferred embodiments of the present invention said material is substantially free of a component that prevents hemolysis said component being selected from the group consisting of tranexamic acid or $\epsilon$-aminocaproic acid.

Thus it will be realized that in some preferred embodiments there is included a selected component that prevents hemolysis, said component selected from the group consisting of tranexamic acid or $\epsilon$-aminocaproic acid chemically immobilized thereon, while in other preferred embodiments said material is substantially free of such component.

In especially preferred embodiments of the present invention, there is provided a hemostatic textile material as hereinabove defined, comprising a plurality of components and wherein the ratios between the components per 1 (one) gram of dialdehyde cellulose is respectively as follows:

| Component | Lower Limit mg | Upper Limit mg | |
|---|---|---|---|
| DAC - oxidation degree | 1.5% | 12% | |
| gelatin | 30 | 100 | |
| chitosan | 50 | 200 | |
| tranexamic acid | 25 | 55 | or |
| $\epsilon$-aminocaproic acid | 30 | 55 | |
| lysozyme | 45 | 55 | or |
| silver nitrate | 4.5 | 5.5 | or |
| Chlorhexidine Hydrochloride (CHX) | 5.0 | 20 | Eqviv. Chlorhexidin gluconate (CHG) Sol. 0.5% up to 2% |
| water | 6.5 ml. | | |

A simple active hemostatic device according to the present invention and based on a dialdehyde cellulose carrier comprises only one ingredient such as chitosan or gelatin by itself, without the other components.

A preferred embodiment of the present invention provides for the key properties of the present invention, which are bleeding stoppage, avoidance of fibrinolysis compounds, and sustaining antimicrobial activity as described herein.

As stated hereinbefore, preferably all the components are dissolved simultaneously in an aqueous medium and, dialdehyde cellulose is kept in the solution for 1.5-2 hours (half as much time as in the known art). Said cellulose, impregnated with said components is then pressed out, air-dried, cut into appropriately sized pads, with the amount of layers per pad and the size of the pad being variable to fill a wide range of requirements. The new proposed material for bleeding stoppage is then sterilized.

BRIEF DESCRIPTION OF THE DRAWINGS

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

In the drawings.

DETAILED DESCRIPTION

Figure 1:
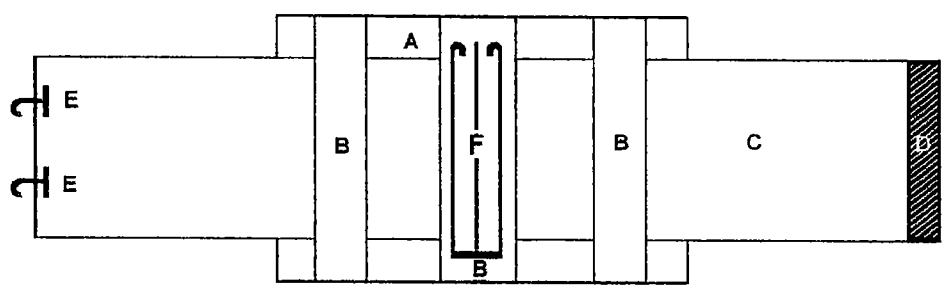
FIG. 1 is a back view of a self-sliding dressing according to the present invention.
Figure 2:
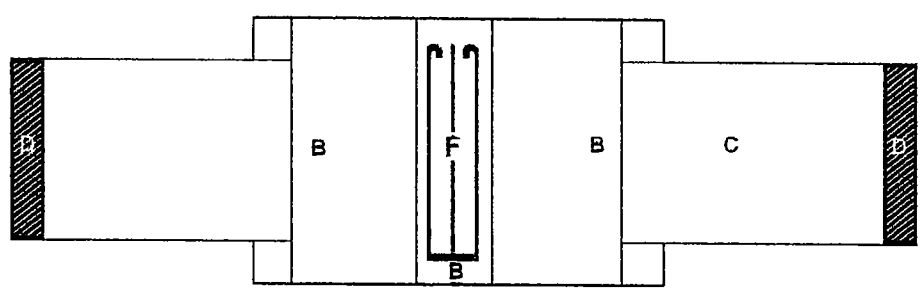
FIG. 2 is a front view of the self-sliding dressing of FIG. 1.

Referring now to FIGS. 1 and 2, there is seen a self-sliding dressing according to the present invention, comprising a pad (A) having a hemostatic textile material incorporated therein by lamination or by sewing or welding. Strips (B) are attached to the backside of pad (A) to enable the sliding of the combined pad (A) on elastic bandage (C). To the remote ends of the elastic bandage (C) there is attached hooks (E) and/or a strip of adhesive tape (D). The self-sliding dressing can also be provided with a pressure and secure buckle (F).

As described hereinbefore, the elastic bandage (C) can be some 40 cm in length while the adhesive strip (D) can be about 5 cm in width. The adhesive tape (D) enables the injured person affix the device to the wound site by himself. Thus, e.g., the adhesive strip (D) is applied to a non-injured skin area near the wound and the combined pad (A) which comprises both a hemostatic and an absorbing layer, is slid along bandage (C) and placed to cover the bleeding wound site. The degree of compression can be adjusted by tension of the elastic bandage wherein two or three turns of the elastic bandage over the combined pad (A) will create the necessary pressure so as to assist bleeding stoppage and will also affix the combined hemostatic dressing pad to the wound site. The pad and bandage can be secured by the adhesive tape (D) or by a Velcro tape or with hooks (E) or by simply knotting the two ends of the bandage (C).

EXAMPLE NO. 1

At room temperature, $\epsilon$-aminocaproic acid (5 g), gelatin (3 g) and lysozyme (0.5 g) are dissolved in distilled water (650 ml). After complete dissolution, dialdehyde cellulose (100 g) with the degree of oxidation of 1.5% in the form of a fabric is immersed in the solution for 1.5 hours and not more than 2 hours. The fabric is then pressed out, and air-dried to a residual humidity of no more than 10%. The treated fabric is then cut into pads, with the amount of layers per pad and the size of the pad being variable to fill a wide range of requirements. For example, a pad of 7.5×5.0 cm made of 4 layers weighs about 1.0 gm. The new proposed material for bleeding stoppage is then sterilized.

EXAMPLE NO. 2

At room temperature, $\epsilon$-aminocaproic acid (5 g), gelatin (6 g) and lysozyme (0.5 g) are dissolved in distilled water (650 ml). After complete dissolution, dialdehyde cellulose (100 g) in the form of a fabric having the degree of oxidation of 12% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 3

At room temperature, ϵ-aminocaproic acid (5 g), gelatin (3 g) and chlorhexidine hydrochloride (0.5 g,) are dissolved in distilled water (650 ml) (formed from 16.25 ml of chlorhexidine gluconate sol. at 20% added to 633.75 ml water to form a total of 650 ml).

After a complete dissolution, dialdehyde cellulose (100 g) in the form of a fabric and having the degree of oxidation of 1.5% is immersed in the solution for 1.5 hours and not more than 2 hours at room temperature, pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 4

At room temperature, ϵ-aminocaproic acid (5 g), gelatin (6 g) and chlorhexidine hydrochloride (2 g) are dissolved in distilled water (650 ml) (formed from 65 ml of chlorhexidine gluconate sol. at 20% added to 585 ml water, i.e. total 650 ml).

After complete dissolution, dialdehyde cellulose (100 g) in the form of a fabric having the degree of oxidation of 12% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 5

At room temperature, ϵ-aminocaproic acid (5 g), gelatin (3 g) and silver nitrate (0.45 g) are dissolved in distilled water (650 ml). After complete dissolution, dialdehyde cellulose (100 g) in form of a fabric having the degree of oxidation of 12% is immersed in the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 6

At room temperature, ϵ-aminocaproic acid (5 g), gelatin (6 g) and silver nitrate (0.7 g) are dissolved in distilled water (650 ml). After complete dissolution, dialdehyde cellulose (100 g) in form of a fabric having the degree of oxidation of 12% is immersed in the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 7

At room temperature, ϵ-aminocaproic acid (5 g), gelatin (3 g) chitosan (2.5 g) and lysozyme (0.5 g) are dissolved in distilled water (650 ml). After complete dissolution, dialdehyde cellulose (100 g) in the form of a fabric having the degree of oxidation of 1.5% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 8

At room temperature, ϵ-aminocaproic acid (5 g), gelatin (6 g), chitosan (20 g) and lysozyme (0.5 g) are dissolved in distilled water (650 ml). After complete dissolution, dialdehyde cellulose (100 g) in the form of a fabric having the degree of oxidation of 12% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 9

At room temperature, ϵ-aminocaproic acid (5 g) gelatin (3 g), chitosan (2.5 g) and chlorhexidine hydrochloride (0.5 g) are dissolved in distilled water (650 ml), equiv. 16.25 ml of chlorhexidine gluconate Sol. at 20% added to 633.75 ml water, i.e. total 650 ml. After complete dissolution, dialdehyde cellulose (100 g) in the form of a fabric and having the degree of oxidation of 1.5% is immersed in the solution, kept for 1.5 hours and not more than 2 hours at room temperature, pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 10

At room temperature, ϵ-aminocaproic acid (5 g), gelatin (6 g), chitosan (20 g) and chlorhexidine hydrochloride (2 g) are dissolved in distilled water (650 ml) equiv. 65 ml of chlorhexidine gluconate Sol. at 20% added to 585 ml water, i.e. total 650 ml. After complete dissolution, dialdehyde cellulose (100 g) in the form of a fabric having the degree of oxidation of 12% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 11

At room temperature, ϵ-aminocaproic acid (5 g), gelatin (3 g), chitosan (2.5 g) and silver nitrate (0.45 g) are dissolved in distilled water (650 ml). After complete dissolution, dialdehyde cellulose (100 g) in form of a fabric having the degree of oxidation of 12% is immersed in the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 12

At room temperature, ε-aminocaproic acid (5 g), gelatin (6 g), chitosan (20 g) and silver nitrate (0.7 g) are dissolved in distilled water (650 ml).

After a complete dissolution, dialdehyde cellulose (100 g) in form of a fabric having the degree of oxidation of 12% is immersed in the solution for 1.5 hours and not more than 2 hours. The fabric is pressed out, air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 13

At room temperature, tranexamic acid (2.5 g), gelatin (3 g) and lysozyme (0.5 g) are dissolved in distilled water (650 ml). After complete dissolution, dialdehyde cellulose (100 g) with the degree of oxidation of 1.5% in the form of a fabric is immersed into the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. For example, a pad of 7.5×5.0 cm made of 4-layers is prepared which weighs about 1.0 gm. The new proposed material for bleeding stoppage is then sterilized.

EXAMPLE NO. 14

At room temperature, tranexamic acid (55 g), gelatin (6 g) and lysozyme (0.5 g) are dissolved in distilled water (650 ml). After complete dissolution, dialdehyde cellulose (100 g) in the form of a fabric having the degree of oxidation of 12% is immersed in the above solution for 1.5 hours and not more than 2 hours. The fabric is pressed out, and air-dried to a residual humidity of no more than 10%, the treated fabric is then cut into pads, with the amount of layers per pad and the size of the pad being variable to fill a wide range of requirements. The new proposed material for bleeding stoppage is then sterilized.

EXAMPLE NO. 15

At room temperature, tranexamic acid (2.5 g) gelatin (3 g) and chlorhexidine hydrochloride (0.5 g) is dissolved in distilled water (650 ml), equiv. 16.25 ml of chlorhexidine gluconate Sol. at 20% added to 633.75 ml water, i.e. total 650 ml.

After complete dissolution, dialdehyde cellulose (100 g) in the form of a fabric and having the degree of oxidation of 1.5% is immersed in the solution, kept for 1.5 hours and not more than 2 hours at room temperature, pressed out, air-dried to a residual humidity of no more than 10%, the layers of the treated fabric are being cut to pads at any amount of layers and at any size requested. The new proposed material for bleeding stoppage is then sterilized.

EXAMPLE NO. 16

At room temperature, tranexamic acid (55 g), gelatin (6 g) and chlorhexidine hydrochloride (2 g) are dissolved in distilled water (650 ml) equiv. 65 ml of chlorhexidine gluconate Sol. at 20% added to 585 ml water, i.e. total 650 ml.

After a complete dissolution, dialdehyde cellulose (100 g) in the form of a fabric having the degree of oxidation of 12% is immersed in the above solution for 1.5 hour and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 17

At room temperature, tranexamic acid (2.5 g), gelatin (3 g) and silver nitrate (0.45 g) are dissolved in distilled water (650 ml). After complete dissolution, dialdehyde cellulose (100 g) in form of a fabric having the degree of oxidation of 12% is immersed in the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 18

At room temperature, tranexamic acid (55 g), gelatin (6 g) and silver nitrate (0.7 g) are dissolved in distilled water (650 ml). After complete dissolution, dialdehyde cellulose (100 g) in form of a fabric having the degree of oxidation of 12% is immersed in the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 19

At room temperature, tranexamic acid (2.5 g), gelatin (3 g) chitosan (2.5 g) and lysozyme (0.5 g) are dissolved in distilled water (650 ml). After complete dissolution, dialdehyde cellulose (100 g) in the form of a fabric having the degree of oxidation of 1.5% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is Then sterilized.

EXAMPLE NO. 20

At room temperature, tranexamic acid (55 g), gelatin (6 g), chitosan (20 g) and lysozyme (0.5 g) are dissolved in distilled water (650 ml). After complete dissolution, dialdehyde cellulose (100 g) in the form of a fabric having the degree of oxidation of 12% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 21

At room temperature, tranexamic acid (2.5 g) gelatin (3 g), chitosan (2.5 g) and chlorhexidine hydrochloride (0.5 g) is dissolved in distilled water (650 ml), equiv. 16.25 ml of chlorhexidine gluconate Sol. at 20% added to 633.75 ml water, i.e. total 650 ml. After complete dissolution, dialdehyde cellulose (100 g) in the form of a fabric and having the degree of oxidation of 1.5% is immersed in the solution, kept for 1.5 hours and not more than 2 hours at room temperature, pressed out, and air-dried to a residual humidity of no more than 10%, the treated fabric is then cut into pads, with the amount of layers per pad and the size of the pad being variable to fill a wide range of requirements. The new proposed material for bleeding stoppage is then sterilized.

EXAMPLE NO. 22

At room temperature, tranexamic acid (55 g), gelatin (6 g), chitosan (20 g) and chlorhexidine hydrochloride (2 g) are dissolved in distilled water (650 ml) equiv. 65 ml of chlorhexidine gluconate Sol. at 20% added to 585 ml water, i.e. total 650 ml. After complete dissolution, dialdehyde cellulose (100 g) in the form of a fabric having the degree of oxidation of 12% is immersed in the above solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 23

At room temperature, tranexamic acid (2.5 g), gelatin (3 g), chitosan (2.5 g) and silver nitrate (0.45 g) are dissolved in distilled water (650 ml). After complete dissolution, dialdehyde cellulose (100 g) in form of a fabric having the degree of oxidation of 12% is immersed in the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 24

At room temperature, tranexamic acid (55 g), gelatin (6 g), chitosan (20 g) and silver nitrate (0.7 g) are dissolved in distilled water (650 ml).

After complete dissolution, dialdehyde cellulose (100 g) in form of a fabric having the degree of oxidation of 12% is immersed in the solution for 1.5 hours and not more than 2 hours. The fabric is pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 25

At room temperature, gelatin (5 g) is dissolved in distilled water (650 ml). Dialdehyde cellulose (100 g) in the form of a fabric and having the degree of oxidation of 1.5% is immersed in the solution, kept for 1.5 hours and not more than 2 hours at room temperature, pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 26

At room temperature, gelatin (10 g)] is dissolved in distilled water (650 ml). Dialdehyde cellulose (100 g) in the form of a fabric and having the degree of oxidation of 12% is immersed in the solution, kept for 1.5 hours and not more than 2 hours at room temperature, pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 27

At room temperature, chitosan (5 g) is dissolved in distilled water (650 ml). Dialdehyde cellulose (100 g) in the form of a fabric and having the degree of oxidation of 1.5% is immersed in the solution, kept for 1.5 hours and not more than 2 hours at room temperature, pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

EXAMPLE NO. 28

At room temperature, chitosan (20 g) is dissolved in distilled water (650 ml). Dialdehyde cellulose (100 g) in the form of a fabric and having the degree of oxidation of 12% is immersed in the solution, kept for 1.5 hours and not more than 2 hours at room temperature, pressed out, and air-dried to a residual humidity of no more than 10%. The treated fabric is then cut into pads, with the amount of layers per pad and the size of the pad being variable to fill a wide range of requirements. The new proposed material for bleeding stoppage is then sterilized.

The proposed hemostatic materials produced as described in the examples hereinabove can be used individually. Alternatively they could also be used in combination with each other, i.e., (1). any of the above hemostatic devices (to be applied to the bleeding wound); (2) any of the absorbing layers; and (3) two different layers which have been attached to each other by sewing or lamination can be used together.

In preferred embodiments of the present invention. the hemostatic materials and materials for bleeding stoppage described in the above examples are attached as part of the front side of a sliding dressing as described herein or, to any roll bandage.

The efficacy of the hemostatic dressings of the present invention has been tested by using a rabbit model and by treating human volunteers. The results are presented hereinafter.

EXAMPLE 29

In a group of volunteers consisting of 25 persons, the hemostatic textile dressings for bleeding stoppage were tested against gunshot injuries and impact wounds accompanied by local bleeding. In all cases, the time elapsed to a complete arrest of bleeding is from 104 to 150 seconds.

TABLE NO. 1

| Examples | Time elapsed to stop bleeding, in seconds | |
|---|---|---|
| | Sample | control |
| Example 29a: Carrier - dialdehyde cellulose degree of oxidation 1.5%, 60 mg of gelatin, 5 mg of lysozyme, 50 mg of ∈-aminocaproic acid per one gram of the carrier | 104 ± 15 | 228 ± 30 |
| Example 29b: degree of cellulose oxidation, 1.5%, 50 mg of gelatin, 30 mg of ∈-aminocaproic acid per one gram of the carrier | 110 ± 30 | 228 ± 30 |
| Example 29c: degree of cellulose oxidation, 12%, 30 mg of gelatin, 5 mg of lysozyme, 50 mg ∈-aminocaproic acid per one gram of the carrier | 113 ± 25 | 228 ± 30 |
| Example 29d: degree of cellulose oxidation, 12%, 5 mg of lysozyme, 30 mg ∈-aminocaproic acid per one gram of the carrier | 127 ± 23 | 228 ± 30 |

The efficacy of the hemostatic dressings of the present invention in terms of bleeding stoppage has been tested on chinchilla rabbits. The results are presented hereinafter.

EXAMPLE 30

Material-Carrier-dialdehyde cellulose-oxidation 1.5%, 30 mg of gelatin, 5 mg of lysozyme, 50 mg ∈-aminocaproic acid per one gram of the carrier The hemostatic materials are designed for a variety of uses, i.e., after dialysis treatment, catheterization, to stop bleeding after surgery, and on the battle field, etc. The efficacy of the hemostatic material has been tested by using different combinations of ingredients and different amount of layers per pad.

Table numbers 2 and 3 show the time elapsed until a complete stoppage of bleeding per different pads having different amount of layers.

Table 2
Effects of the hemostatic material on blood arrest in experiments on chinchilla rabbits
Test Article:
Carrier-dialdehyde cellulose-oxidation 1.5%, 30 mg of gelatin, 5 mg of lysozyme, 25 mg of tranexamic acid per one gram of the carrier

| Preparation | The number of Chinchilla Rabbits | Preparations - Time elapsed to bleeding arrest (sec) |
|---|---|---|
| Sample #1 (3-layers per pad) | 7 | 106 ± 9 |
| Sample # 2 (5-layers per pad) | 7 | 87 ± 17 |
| Sample # 3 (7-layers per pad) | 7 | 58 ± 12 |
| Control | 7 | 228 ± 30 |

Table 3
Effects of the hemostatic material on blood arrest in experiments on 7 chinchilla rabbits
Test Article:
Carrier-dialdehyde cellulose-oxidation 12%, 30 mg of gelatin, 50 mg of chitosan, 5 mg of lysozyme, 25 mg of tranexamic acid per one gram of the carrier

| Preparation | The number of Chinchilla Rabbits | Preparations - Time elapsed to bleeding arrest (sec) |
|---|---|---|
| Sample #1 (2-layers) | 7 | 101 ± 7 |
| Sample # 2 (3-layers) | 7 | 82 ± 15 |
| Sample # 3 (5-layers) | 7 | 55 ± 10 |
| Control | 7 | 228 ± 30 |

EXAMPLE 31

Material-Carrier-dialdehyde cellulose-oxidation 1.5%, 30 mg of gelatin, 5 mg of lysozyme, 50 mg ∈-aminocaproic acid per one gram of the carrier In a group of volunteers consisting of 48 subjects, hemostatic material for arresting bleeding after dialysis, was tested against the puncture wound created for dialysis. Said hemostatic material (sample 1) was composed of: a material carrier comprising dialdehyde cellulose-oxidation 1.5%; and gelatin 30. mg., ∈-aminocaproic acid 50 mg., and lysozime 5 mg. per one gram of carrier. In 35 cases, by using a 7 (seven) layer sample the time elapsed to a complete bleeding arrest did not exceed 78 seconds.

TABLE NO. 4

| Preparation Amount of layers | Number of treated volunteers | Time elapsed to stop bleeding, in seconds |
|---|---|---|
| Sample #1 (3-layers per pad) | 3 | 110 ± 7 |
| Sample # 2 (5-layers per pad) | 6 | 92 ± 19 |
| Sample # 3 (7-layers per pad) | 35 | 63 ± 14 |
| Control | 4 | 193 ± 13 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A hemostatic textile material to stop bleeding comprising:
   a) a dialdehyde cellulose carrier wherein the degree of oxidation of the dialdehyde cellulose varies from about 1.5% to 12%; and
   b) a selected component that prevents hemolysis, said component selected from the group consisting of tranexamic acid and ∈-aminocaproic acid chemically immobilized thereon; and
   c) a blood coagulation factor selected from the group consisting of chitosan and gelatin, said blood coagulation factor being chemically immobilized thereon, and further optionally comprising:

d) a bacteriolytic agent selected from the group consisting of a lysozyme enzyme, silver nitrate, and chlorhexidine, wherein the aldehydic groups of said dialdehyde cellulose carrier are spread equally and uniformly onto and into said dialdehyde cellulose carrier allowing only up to 85-90% covalent bonding with amino groups of said blood coagulation factor.

2. A hemostatic textile material according to claim 1 wherein said textile material is free of one component selected from the group consisting of tranexamic acid and ε-aminocaproic acid.

3. A hemostatic textile material according to claim 1 comprising 30 to 100 mg gelatin; 50 to 200 mg chitosan; 25 to 55 mg tranexamic acid or 30 to 55 mg ε-aminocaproic acid; 4.5 to 5.5 mg lysozyme, 4.5 to 5.5 mg silver nitrate, 5.0 to 20 mg chlorhexidine hydrochloride or 0.5% to 2% chlorhexidine gluconate; and 6.5 ml water for each gram of dialdehyde cellulose, wherein the dialdehyde cellulose has a degree of oxidation of 1.5 to 12%.

4. A sliding pressure dressing device incorporating a hemostatic textile material according to claim 1 wherein said hemostatic textile material is incorporated into a pad provided with attachment means for sliding engagement on an elastic bandage.

5. A sliding pressure dressing device according to claim 4 wherein said hemostatic textile material is incorporated into said sliding pad by sewing.

6. A sliding pressure dressing device according to claim 4 wherein said hemostatic textile material is incorporated into said sliding pad by lamination.

7. A process for the preparation of a hemostatic textile material to stop bleeding, said hemostatic textile material comprising a dialdehyde cellulose carrier wherein the degree of oxidation of the dialdehyde cellulose varies from about 1.5% to 12%; and a blood coagulation factor selected from the group consisting of chitosan and gelatin; said blood coagulation factor being chemically immobilized thereon, wherein the aldehydic groups in said dialdehyde cellulose carrier allow only up to 85-90% covalent bonding with amino groups of said blood coagulation factor; said method comprising:
   a. immersing a textile material in a solution containing aldehyde functional groups;
   b. pressing said textile material in a wringer to spread said aldehyde functional groups equally and uniformly onto and into said textile material to form said dialdehyde cellulose carrier;
   c. air drying said dialdehyde cellulose carrier;
   d. bringing said dialdehyde cellulose carrier into contact with a solution of said blood coagulation factor;
   e. pressing said dialdehyde cellulose carrier in a wringer to spread said blood coagulation factor equally and uniformly onto and into said dialdehyde cellulose carrier; and
   f. drying said dialdehyde cellulose carrier.

8. A hemostatic textile material prepared according to the process of claim 7.

9. A hemostatic textile material according to claim 8 wherein said hemostatic textile material comprises a component that prevents hemolysis being selected from the group consisting of tranexamic acid, ε-aminocaproic acid, and mixtures thereof.

10. The hemostatic textile material of claim 9 comprising said chitosan and said gelatin.

11. The hemostatic textile material of claim 9 comprising said gelatin.

12. The hemostatic textile material of claim 9 being free of one of said tranexamic acid and said ε-aminocaproic acid.

13. The hemostatic textile material of claim 12 comprising said ε-aminocaproic acid.

14. The hemostatic textile material of claim 8 being fibrinogen-free and thrombin-free.

15. The process of claim 7 performed without fibrinogen and without thrombin.

16. A hemostatic textile material according to claim 2 comprising said ε-aminocaproic acid.

17. A hemostatic textile material according to claim 1 being fibrinogen-free and thrombin-free.

18. A hemostatic textile material according to claim 1 comprising:
   said ε-aminocaproic acid;
   said gelatin; and
   said lysozyme enzyme.

19. A hemostatic textile material according to claim 1 comprising only one of said lysozyme enzyme, silver nitrate, and chlorhexidine.

* * * * *